United States Patent [19]
Mowery, Jr.

[11] Patent Number: 4,824,446
[45] Date of Patent: Apr. 25, 1989

[54] GAS CHROMATOGRAPHY SIMULATION

[75] Inventor: Richard A. Mowery, Jr., Bartlesville, Okla.

[73] Assignee: Applied Automation, Inc., Bartlesville, Okla.

[21] Appl. No.: 196,720

[22] Filed: May 23, 1988

[51] Int. Cl.$^4$ .................... B01D 15/08; G01N 30/02
[52] U.S. Cl. .......................................... 55/67; 55/386; 73/23.1; 422/89
[58] Field of Search ............. 55/67, 197, 386; 73/23.1; 210/656; 422/89

[56] References Cited

U.S. PATENT DOCUMENTS

| | | | |
|---|---|---|---|
| 3,307,333 | 3/1967 | Norem et al. | 55/197 |
| 3,719,084 | 3/1973 | Walker | 55/197 X |
| 3,822,203 | 7/1974 | Annino et al. | 55/67 X |
| 3,863,489 | 2/1975 | Ayers et al. | 73/23.1 |
| 3,896,659 | 7/1975 | Goodman | 55/67 X |
| 4,579,663 | 4/1986 | Poile et al. | 210/656 |
| 4,719,017 | 1/1988 | Uchino et al. | 55/67 X |
| 4,757,023 | 7/1988 | Trestianu et al. | 55/386 X |

FOREIGN PATENT DOCUMENTS

| | | | |
|---|---|---|---|
| 135242 | 4/1979 | German Democratic Rep. | 55/386 |
| 22261 | 5/1986 | Japan | 55/386 |

OTHER PUBLICATIONS

Giddings, "Optimum Conditions for Separation in Gas Chromatography", Analytical Chemistry, vol. 32, No. 12, Nov. 1960, pp. 1707–1711.

Primary Examiner—Robert Spitzer
Attorney, Agent, or Firm—Laney, Dougherty, Hessin & Beavers

[57] ABSTRACT

A linear equation which infers elution time in a gas chromatograph as a function of temperature is assigned to a chemical compound. The linear equation is useful in constructing a computer data base which contains a long list of chemical compounds, a list of chromatographs each having a separation column containing a different adsorbent material, and a long list of linear equations associating each chemical compound with each chromatograph. The data base, which is arranged for computer searching, aids researchers in gas chromatography by automating a systematic search for optimum combination of separation columns and operating parameters.

11 Claims, 8 Drawing Sheets

GAS CHROMATOGRAPHY SIMULATION

This invention relates to gas chromatography. In one aspect, it relates to a method for finding the optimum choice of separating column and operating parameters to achieve a separation by gas chromatography. In another aspect it relates to a method for the characterization of chemical compounds. In yet another aspect it relates to a method for the identification of chemical compounds.

BACKGROUND OF THE INVENTION

The gas chromatograph is perhaps the most useful analytical tool available today to the chemist. The gas chromatograph takes a fixed volume of sample gas, or liquid which can be vaporized, and introduces the fixed volume of sample into a separating column which contains a stationary phase of adsorbent material. The sample is transported through the separating column using a mobile phase carrier, and individual molecules of the sample gas are adsorbed and then released at different times from the adsorbent stationary phase material in the column.

When the adsorbent material in the separating column and the operating parameters are properly selected, the separated components of interest elute or emerge from the column completely separated from each other and from any other component that may be present. This eluting stream is passed through a detector and the relative response of the detector is sensed by an electronic unit and recorded as a peak on a chart. This chart is referred to as a chromatogram.

Experience has shown that depending on the chemical components to be separated, a specific type of separating column, column temperature, flow rate, film thickness and other operating parameters will produce a more satisfactory result than other columns and operating parameters. As used herein the type of column refers to the particular adsorbent material contained in the column in addition to the manner in which the column is operated i.e. a capillary column or a packed column.

While one can conceivably find an optimum combination of column type and operating parameters for a nonroutine separation by making trial and error injection, or by searching literature for various retention data tables, this is not particularly satisfactory because the time required to establish an optimum combination for the particular separation is often excessive. In most cases, these latter approaches are only starting points for a nonroutine separation in which the chromatographer must still adjust several parameters to make the desired separation. In some cases, such adjustments can require several days of laboratory work.

Over the years there has developed the need for a low cost technique that would simply permit the selection of operating parameters and column type that will simulate a gas chromatograph within a few minutes.

Accordingly, it is an object of the invention to provide a method for automatically predicting the characteristics of a gas chromatographic separation for a given type of column with given operating parameters.

It is another object of this invention to provide a method for the characterization of a chemical compound which will predict its chromatographic elution time.

It is yet another object of this invention to provide a method for the identification of a chemical compound from its experimentally determined chromatographic elution time.

It is a further object of this invention to store elution data for a substantial number of chemical compounds in a memory space compatible with a personal computer.

BRIEF SUMMARY OF THE INVENTION

In accordance with the present invention there is provided a method for constructing a simplified computer data file and retrieval system to aid researchers in gas chromatography by automating a systematic search for optimum combinations of operating parameters and separating columns over a given temperature range. A typical data file contains elution time data for about 2,000 organic compounds for use with 5 preferred stationary phases of adsorbent material. This substantial volume of data, which is stored in a memory size compatible with most personal computers, is input into the computer in a format which permits searching and retrieval of the data.

The data storage in a personal computer is based on the discovery that a large number of chemical compounds can be assigned a unique linear characteristic equation that infers its elution time in a gas chromatograph for a given stationary phase over a given temperature range. Thus, the only data necessary for characterizing compounds are the constants required in the characteristic equation. The required constants are stored in the computer memory and are retrieved to calculate retention time for a desired compound. The unique characteristic equation is of the form:

$$\text{Log}(S) = a_1 T_1 + b_1 \tag{1A}$$

where:

$a_1$ and $b_1$ are experimentally determined constants,
$T_1$ is the separation column temperature in °C., and
S is a defined parameter dependent on the carbon number C and the distribution coefficient $K_n$ given by the following equation:

$$S = \text{Log}(K_n)/C \tag{2A}$$

If desired the step of dividing the log ($K_n$) by the carbon number C to define the parameter S in equation (2A) may be omitted, and a parameter M may be defined according to equation (2B):

$$M = \text{Log}(K_n) \tag{2B}$$

where $K_n$ is defined above.

Using the M parameter, an alternative equation that infers the elution time in a manner similar to Equation (1A) is of the form:

$$\text{Log}(M) = a_2 T_1 + B_2 \tag{1B}$$

where: $a_2$ and $b_2$ are experimentally determined constants, and $T_1$ is defined above.

Using either Equation (1A) or (1B) a large number of organic and inorganic compounds are characterized and the appropriate values for the constants $a_1$ and $b_1$, or $a_2$ and $b_2$, are stored in the computer data file. By searching the data file and then making appropriate calculations, the user can automatically obtain a simulated chromatogram showing the elution of components of interest from a specified type of column, or can automatically obtain an optimum combination of separating column and operating parameters for a specified separation, or alternately can obtain a list of compounds having a specified chromatographic retention time for a specified column type.

Other objects and advantages of the invention will be apparent from the foregoing brief description of the invention and the claims as well as the detailed description of the drawings which are briefly described as follows:

DETAILED DESCRIPTION OF THE DRAWINGS

DETAILED DESCRIPTION OF THE INVENTION

Figure 2A:
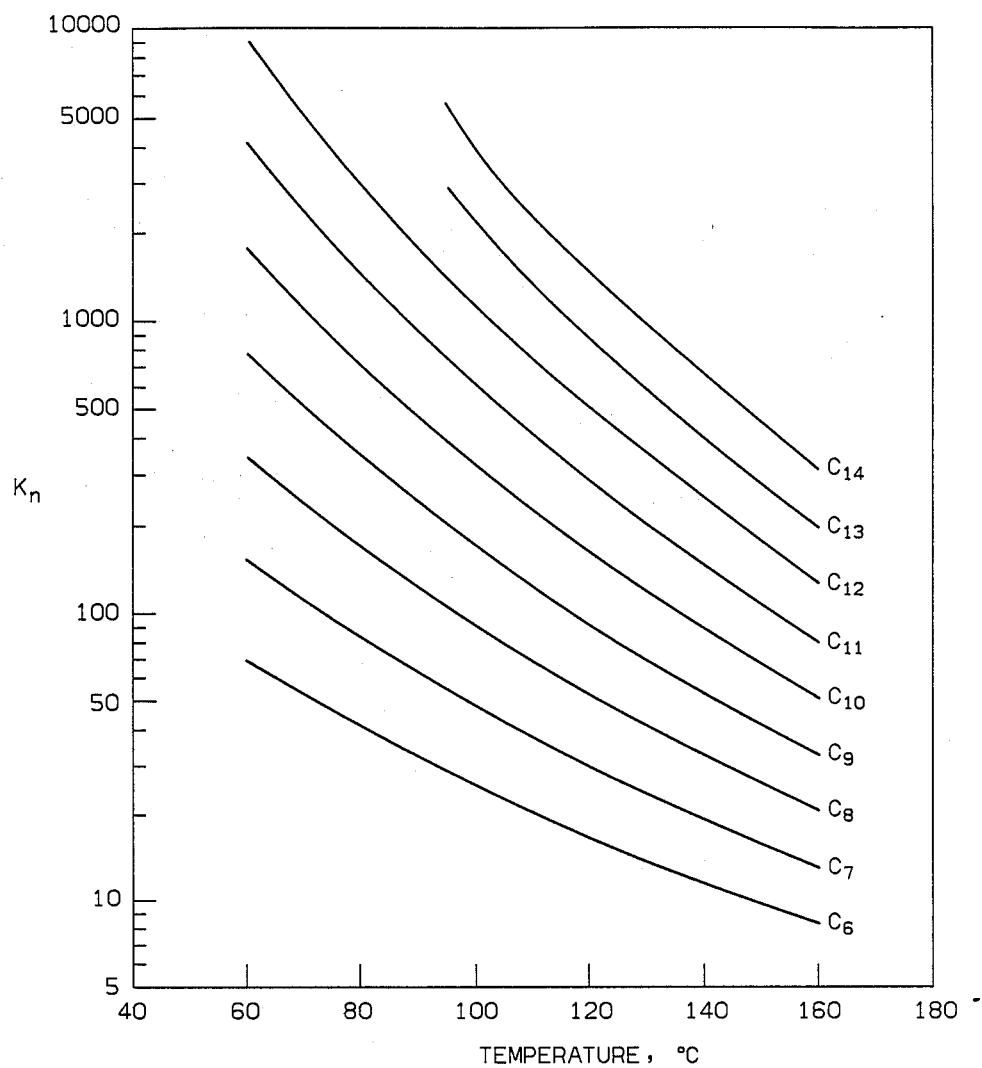
FIG. 2A is a plot of Log ($K_n$) as a function of temperature for a series of n-alkanes.
Figure 2B:
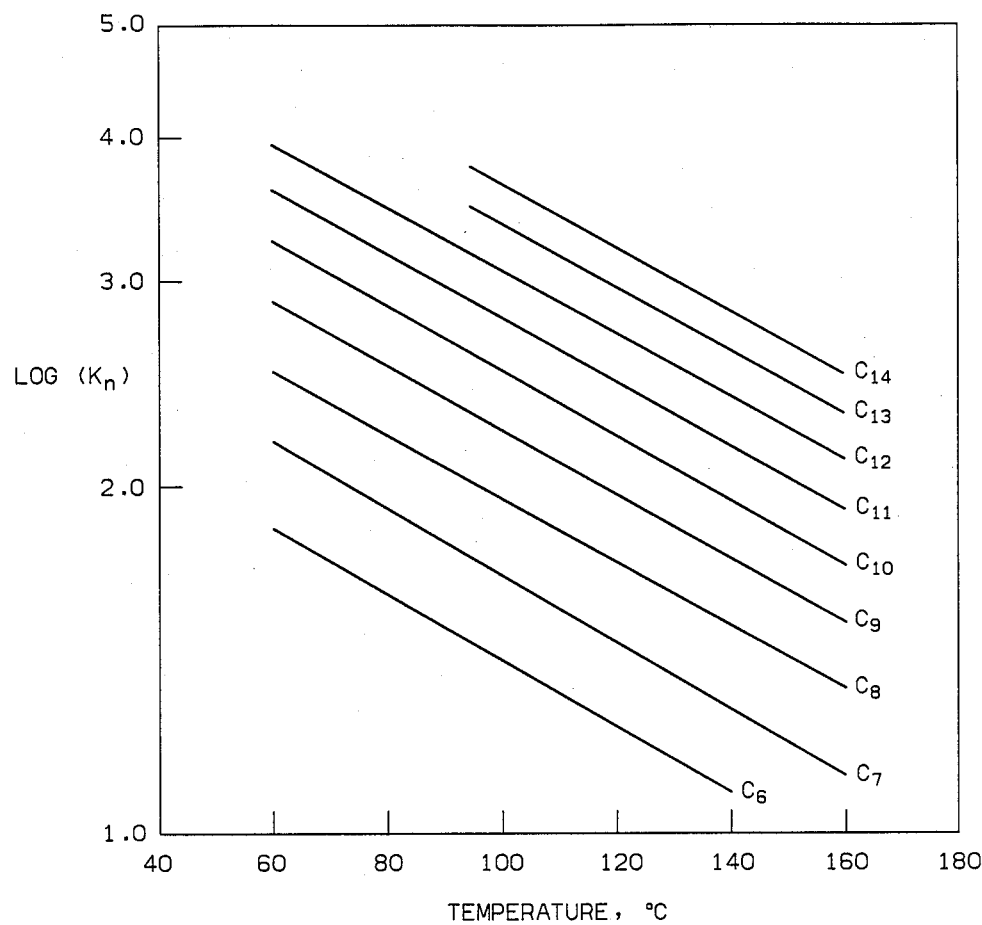
FIG. 2B is a plot of the defined parameter M as a function of temperature for a series of n-alkanes.
Figure 2C:
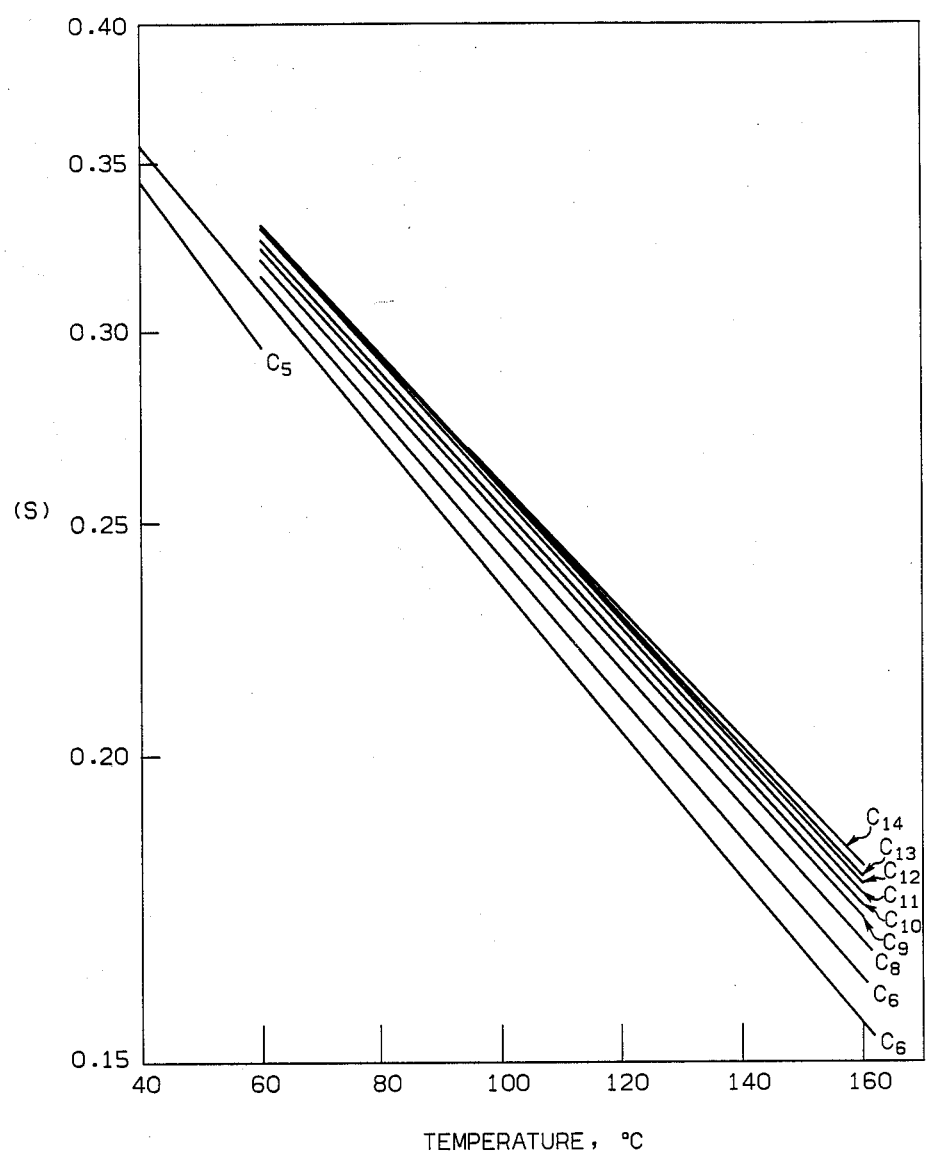
FIG. 2C is a plot of the defined parameter S as a function of temperature for a series of n-alkanes.

For a better understanding of the invention the derivation of the characteristic equations (1A) and (1B), along with the necessary conditions for obtaining data illustrated in the plot in FIG. 2B or 2C, is present below.

The elution time of a nonretained chromatographic peak is defined as $t_o$, which is simply the time it takes a nonretained peak, normally air, to travel from the injector to the detector. The time $t_o$ is equal to the distance of the path length of the column system divided by the average linear velocity of the carrier gas. In other words, a component with a retention time of $t_o$ simply spends all of its time between the injection and the detector in the mobile phase.

Most components when injected do spend a finite amount of time in the stationary phase of the column as they move through the column. The time a component (n) spends in the stationary phase is called the adjusted retention time and is equal to the elution time $t_n$ of component (n) minus the time of the nonretained peak $t_o$. All components spend the same amount of time in the mobile phase equal to $t_o$ but for a separation to occur, a different amount of time must be spend in the stationary phase. Therefore, one of the basic concepts of gas chromatograph is a ratio of the amount of time a component spends in the stationary phase to the amount of time the component spends in the mobile phase, or:

$$(t_n - t_o)/t_o = k_n \quad (3)$$

In Equation (3) $k_n$ is this ratio, often called the capacity factor or partition ratio for component (n). The International Union of Pure and Applied Chemistry recommends the term "mass distribution ratio" in preference to either term. More importantly, $k_n$ can be related to the more fundamental thermodynamic distribution coefficient $K_n$. The significance of $K_n$ will become apparent hereinbelow. A rearrangement of Equation (3) into Equation (4) shows that the adjusted retention time is equal to the product of $k_n$ and $t_o$.

$$t_n - t_o = t_o k_n \quad (4)$$

Thus, any change in the adjusted retention time of component (n) must be the result of a change in this product. The partition ratio is temperature dependent and will remain constant as long as the column temperature remains constant. Changes in $t_o$ are brought about by any change in the ratio of the path length of the column system (L) to average linear velocity ($\mu$), since:

$$t_o = L/\mu$$

The resulting ratio and not necessarily the individual values for (L) or ($\mu$) is significant, although certainly both (L) and ($\mu$) must be operated within practical limits. Likewise, the average linear velocity ($\mu$) is dependent upon other factors such as the compressibility factor, however, since the retention time depends directly upon the values for $t_o$ and $k_n$, the individual values of (L) and ($\mu$) must be within certain ratio limits to provide a $t_o$ that is compatible with the efficiency and analysis time requirements.

For wide-bore capillary columns, one guideline for determining ($\mu$) is that the flow rate be around 2.5 mL/min. for an average ($\mu$) of ca 0.2 meters/sec., for highest column efficiency; 10 mL/min. average ($\mu$) or ca 0.7 meters/sec. for best general operation of the column, or about 30 mL/min. average ($\mu$) ca 2 meters/sec. for fastest analysis time.

A wide-bore column, when operated to provide the fastest analysis, will also have about an order of magnitude fewer number of theoretical plates than the same column when operated for highest efficiency (the latter has approximately 2,100 theoretical plates/meter). However, it should be noted that even when operated for fastest analysis, a 50 meter wide-bore capillary column typically provides more than twice the number of theoretical plates than found with the standard 6 ft.×2 mm i.d. packed column.

In addition, wide-bore capillary columns generally have a sufficient number of theoretical plates to permit the chromatographer to essentially "tune in" the efficiency requirements for a particular separation. In a sense, any extra efficiency should be "traded-in" by operating the column at a higher carrier flow rate which provides a shorter analysis time. The significant point is that for a defined length of time, a ($t_o$) can be approximated with a ($\mu$) that reflects the general requirements necessary to make the desired separation.

In most cases, as long as the value of $t_o$ provides the approximate desired efficiency, the adjusted retention time should first be varied by a change in $k_n$ rather than a change in $t_o$. Thus, in order to simulate a chromatogram, an initial $t_o$ can be defined as an input statement to a computer program which will reflect the approximate efficiency and time requirements of the separation. Once this $t_o$ is defined, then a realistic simulation can be generated that is based on $k_n$ and temperature. In turn, if the initial simulation does not entirely meet the chromatographers needs, then additional simulations can be easily generated by first changing $k_n$ and then if necessary modifying $t_o$.

It was previously mentioned that $k_n$ was related to the more fundamental distribution coefficient or constant $K_n$. The relationship is shown in equation (6) in which ($\beta$) is related to the openness of the column and the percent loading of the stationary phase.

$$k_n = K_n/\beta \tag{6}$$

$\beta$ is called the phase ratio since it is a ratio of the volume occupied by the gas phase to that volume occupied by the liquid stationary phase. The significance of $K_n$ is that it is a true equilibrium constant and is only governed by the compound (n), the stationary phase, and the temperature.

As shown in equation (6), the value for $k_n$ depends upon the ratio $K_n$ to $\beta$, in which $\beta$ typically has values between 5 and 35 for packed columns; however, packed column $\beta$ values are generally not readily available for use in equation (6). In contrast, the determination of a $\beta$ value for capillary columns can be calculated from equation (7A); or in many cases, where $d \gg r$, equation (7B).

$$\beta = (r = 2d)/2(d) \tag{7A}$$

$$\beta = (r)/2(d) \tag{7B}$$

where (r) is the inner radius of the column and (d) is the film thickness of the stationary phase. Phase ratio values for capillary columns typically range from about 50 to 1,500, with a much smaller number of preferred ratios for $\beta$.

If a void volume time $t_o$ and the phase ratio $\beta$ are defined as an input parameter to a computer system, then the simulation will depend only on the value of $K_n$ for each compound at the desired column temperature, and retention data can be obtained for each of five groups of preferred stationary phases stored in the computer. The classical equation tht commonly relates the $K_n$ value to temperature is shown in equation (8).

$$\text{Log } (K_n) = a/T_1 + b \tag{8}$$

where (a) and (b) are considered constants and $T_1$ is the temperature in degrees Kelvin (°K.).

It is noted that equation (8) can be used to simulate the chromatograms, however, an alternative approach is preferred in the present invention.

FIG. 2A shows a graph of log ($K_n$) as a function of temperature in degrees centigrade for a series of n-alkanes. As illustrated the resulting curves are nonlinear and can be represented by a general expression of the form:

$$\text{Log } (K_n) = b_o(10)a_oT \tag{9}$$

where $a_o$ and $b_o$ are constants and (T) is the column temperature in degrees Centigrade.

As shown in equation (10) and FIG. 2B a series of "linear plots" are obtained if the Log of (Log $K_n$) is plotted versus temperature. These "linear plots" are really logarithmic values that are mapped in a linear domain and have a general expression:

$$\text{Log } [\text{Log } (K_n)] = a_oT + b_1 \tag{10}$$

or since log $(K_n) = M$ $$\text{Log } (M) = a_2T_1 + b_2 \tag{1B}$$

Equation (1B) is also a basic relationship which could be used to characterize the compounds and simulate a chromatogram, however, if desired one additional step can be included. The carbon number is included as part of the basic expression for a parameter S defined as:

$$S = \text{Log } (K_n)/C \tag{2A}$$

where C is the carbon number of the compound of interest. In equation (2A) dividing log ($K_n$) by the compounds carbon number only results in the expression having a different set of values for the constants $a_2$ and $b_2$ compared to $a_1$ and $b_1$ in Equation (1A). In turn, if equation (9) is converted with the appropriate constants to its logarithmic form and expressed in terms of equation (2A), then the following expression is obtained:

$$\text{Log } (S) = a_1T_1 + b_1 \tag{1A}$$

where $a_1$ and $b_1$ are constants for the particular compound and stationary phase, and $T_1$ is the column temperature in degrees Centigrade °C.

One interesting aspect of using this approach to simulate a chromatogram is that the carbon number is a known parameter that can be used as part of the input statement to the data file. In this manner, the response time of the computer system is faster since only those compounds with the correct carbon number need to be searched in the data file system.

Using the carbon number in the basic expression also has the effect of normalizing the various individual expressions into a small range of values as illustrated in FIG. 2C, which in some cases may be useful for predicting compounds that are not in the computer file. For the temperatures ranges used, the S values were generally between 0.2-0.6. Consequently, Log (S) is a negative number whose absolute magnitude increases as S decreases.

EXAMPLES

The plots presented in FIG. 2C, for the chromatographic characterization of n-alkane is on OV-101 stationary phase of poly(dimethylsiloxane), illustrate the relationship between the previously defined parameter S and temperature for a series of n-alkanes. These plots were obtained using the equipment illustrated in FIG. 1.

Equipment Used:

| | |
|---|---|
| Chromatograph System including programmer 24, oven 12, and detector 16. | Model 2100, OPTICHROM ® gas Chromatograph System from Applied Automation, Inc., Bartlesville, Oklahoma. |
| Column 10 | Capillary type, 50 meters X .53 mm i.d. from Quardex Corp., New Haven, Connecticut. |
| Column stationary phase | OV-101, poly(dimethylsiloxane) |
| Column film thickness | $1 \times 10^{-6}$ meters. |
| Carrier gas 22 | He |
| Detector 16 | Flame ionization type. |
| Injection 20 | 0.5 mL MAT injection valve from Mess and Apparatetechnik, Mumr, West Germany. |
| Recorder 18 | Model 5601-S from Easterline Angus, Indianapolis, Indiana. |

Figure 1:
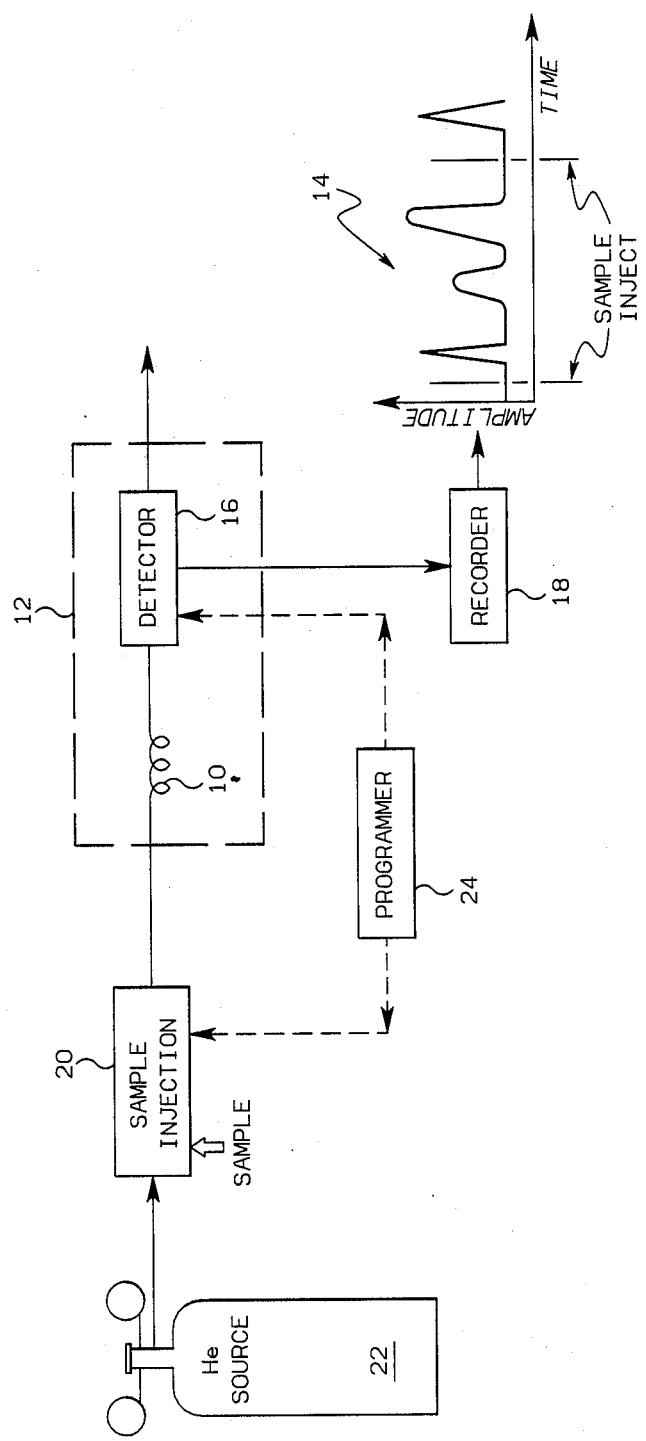
FIG. 1 is a simplified illustration of a basic chromatograph system.

Referring now to FIG. 1 with the column 10, located in oven 12, stabilized at the desired temperature, chromatograms 14 for the components of interest and for a nonretained component were obtained.

From the chromatogram 14, the retention time of each component $t_n$ and the retention time for a nonretained component were recorded for a number of operating temperatures. Normally two separate injections at different carrier flow rates were recorded for each temperature point selected over the operating temperature range. It is noted that a change in the carrier flow rate verified that the resulting $k_n$ values were essentially independent of the carrier velocity.

In turn, an average $k_n$ value based on at least two injections for each of the components was calculated from equation (3), and the distribution coefficient $K_n$ is calculated from equation (6). Once the distribution coefficients $K_n$ for a component was determined, equation (2A) was used to relate the log of $K_n$ to its S value.

At this point, S was plotted versus temperature on a semi-log scale as illustrated in FIG. 2C. The constant $a_1$ for the slope of equation (1A) and the constant $b_1$ for the intercept are determined from a least squares fit of a straight line equation to the data plotted in FIG. 2C. The procedure is essentially the same for determining the constants $a_2$ and $b_2$ for an M plot illustrated in FIG. 2B.

The above-described equipment and method for calculating the S parameter has been applied to an assortment of organic compounds as listed in Table 1. Table 1 includes the constants for the linear equation for log (S) as a function of temperature for the assortment of compounds listed in column 2. Column 4 lists the experimental temperature range over which the data was collected.

TABLE 1

The Log (S) Values for Assorted Compounds on an OV101 Liquid Stationary Phase

| Carbon Number | Compound Name | Log(S) = | Temperature Range (°C.) |
|---|---|---|---|
| 5 | n-Pentane | −0.00320T−0.3391 | 42.2–60.5 |
| 5 | t-Pentene 2 | −0.00334T−0.3260 | 40.0–50.0 |
| 5 | c-Pentene 2 | −0.00323T−0.3223 | 40.0–60.0 |
| 5 | 1-Pentene | −0.00300T−0.3585 | 26.7–140.0 |
| 5 | Cyclopentane | −0.00296T−0.2857 | 40.0–60.0 |
| 5 | 2Methylbutane | −0.00283T−0.3828 | 40.6–127.8 |
| 6 | n-Hexane | −0.00291T−0.3380 | 40.0–160.0 |
| 6 | 1-Hexene | −0.00293T−0.3465 | 26.7–140.0 |
| 6 | Methylcyclopentane | −0.00285T−0.3167 | 60.0–80.0 |
| 6 | Cyclohexane | −0.00277T−0.2952 | 60.0–80.0 |
| 6 | Benzene | −0.00258T−0.3163 | 60.0–148.9 |
| 6 | 2Methylpentane | −0.00282T−0.3691 | 40.6–127.8 |
| 6 | 3Methylpentane | −0.00286T−0.3541 | 40.6–127.8 |
| 7 | n-Heptane | −0.00285T−0.3330 | 60.5–160.0 |
| 7 | 1-Heptene | −0.00291T−0.3372 | 26.7–140.0 |
| 7 | 2Methylhexane | −0.00282T−0.3561 | 40.6–127.8 |
| 7 | 3Methylhexane | −0.00285T−0.3484 | 40.6–127.8 |
| 7 | 2,3Dimethylpentane | −0.00289T−0.3493 | 60.0–80.0 |
| 7 | Methylcyclohexane | −0.00271T−0.3227 | 60.0–90.0 |
| 7 | Toluene | −0.00259T−0.3128 | 60.0–148.9 |
| 8 | n-Octane | −0.00276T−0.3330 | 60.0–160.0 |
| 8 | 1-Octene | −0.00282T−0.3343 | 26.7–140.0 |
| 8 | Ethylbenzene | −0.00254T−0.3195 | 60.0–148.9 |
| 9 | n-Nonane | −0.00274T−0.3285 | 60.0–160.0 |
| 9 | Propylbenzene | −0.00254T−0.3226 | 60.0–148.9 |
| 10 | n-Decane | −0.00271T−0.3259 | 60.0–160.0 |
| 10 | Butylbenzene | −0.00254T−0.3216 | 60.0–148.9 |
| 11 | n-Unicane | −0.00269T−0.3240 | 60.0–160.0 |
| 12 | n-Dodecane | −0.00267T−0.3236 | 60.0–160.0 |
| 13 | n-Tridecane | −0.00265T−0.3234 | 60.0–160.0 |
| 14 | n-Tetradecane | −0.00264T−0.3230 | 60.0–160.0 |

Tables 2 and 3 show the log (S) results of a series of n-alkanes separated on a Carbowax 20M column, and on an OV17 liquid stationary phase respectively. The experimental data obtained for constructing Tables 2 and 3 and the format of the data is the same as for Table 1. Table 2 indicates that components with wide ranges in polarity do not affect the log (S) expression to simulate their retention characteristics.

Table 4 shows the log (M) results of a series of n-alkanes on an OV101 liquid stationary phase.

TABLE 2

The Log(S) Values for Assorted n-Alkanes on a Carbowax 20 M Liquid Stationary Phase

| Carbon Number | Compound Name | Log(S) = | Temperature Range (°C.) |
|---|---|---|---|
| 8 | n-Octane | −0.00287T−0.5020 | 62.2–138.3 |
| 9 | n-Nonane | −0.00293T−0.4734 | " |
| 10 | n-Decane | −0.00285T−0.4749 | " |
| 11 | n-Undecane | −0.00280T−0.4567 | " |
| 12 | n-Dodecane | −0.00279T−0.4470 | " |
| 13 | n-Tridecane | −0.00276T−0.4405 | " |
| 14 | n-Tetradecane | −0.00273T−0.4345 | " |

Column: 50 meters × 0.53 mm i.d. fused silica capillary column containing a bonded 1 μm film of Carbowax 20 M, a poly (alkyleneoxide).

TABLE 3

The Log(S) Values for Assorted n-Alkanes and n-Alcohols on an OV17 Liquid Stationary Phase

| Carbon Number | Compound Name | Log(S) = | Temperature Range (°C.) |
|---|---|---|---|
| 8 | n-Octane | −0.00308T−0.3777 | 62.2–168.3 |
| 9 | n-Nonane | −0.00300T−0.3692 | " |
| 10 | n-Decane | −0.00296T−0.3616 | " |
| 11 | n-Undecane | −0.00290T−0.3573 | " |
| 12 | n-Dodecane | −0.00285T−0.3554 | " |
| 13 | n-Tridecane | −0.00281T−0.3539 | " |
| 14 | n-Tetradecane | −0.00278T−0.3521 | " |
| 6 | 1-Hexanol | −0.00296T−0.1643 | 79.4–168.3 |
| 7 | 1-Heptanol | −0.00287T−0.1846 | " |
| 8 | 1-Octanol | −0.00282T−0.2004 | " |
| 9 | 1-Nonanol | −0.00279T−0.2109 | " |
| 10 | 1-Decanol | −0.00277T−0.2195 | " |

Column: 50 meters × 0.53 mm i.d. fused silica capillary column containing a 1 μm film of OV-17, a poly(50-methyl/50 phenylsiloxane).

TABLE 4

The Log(M) Values for Assorted n-Alkanes on an OV101 Liquid Stationary Phase

| Compound Name | Log(M) = | Temperature Range |
|---|---|---|
| n-Pentane | 0.3565−0.003153T | 30–100 |
| n-Hexane | 0.4465−0.003018T | 30–100 |
| n-Heptane | 0.5200−0.002937T | 30–100 |
| n-Octane | 0.5860−0.003006T | 30–100 |
| n-Nonane | 0.6251−0.002691T | 30–200 |
| n-Decane | 0.6704−0.002635T | 40–200 |
| n-Undecane | 0.7034−0.002547T | 100–200 |
| n-Dodecane | 0.7409−0.002519T | 100–200 |
| n-Tridecane | 0.7772−0.002506T | 100–200 |
| n-Tetradecane | 0.8107−0.002500T | 100–200 |
| n-Pentadecane | 0.8386−0.002473T | 100–200 |

Column: 50 meters × 0.53 mm i.d. fused silica capillary column containing a 1 μm film of OV101, a poly(dimethylsiloxane).

As a practical matter for building a data file that is compatible with most personal computers, about 2,000 compounds can be characterized using equations (1A) or (2A). These compounds can be characterized for 5 different preferred stationary phases as listed in Table 5 below. Several authors have indicated that this group of 5 preferred stationary phases will accommodate more than 80% of the required separations in gas chromatography.

TABLE 5
Preferred Liquid Stationary Phases (1) A poly(dimethylsiloxane), such as SP2100, OV-1, OV-101 or SE 30 GC grade.
(2) A poly(50%-methyl/50%-phenylsiloxane), such as OV-17 or SP-2250.
(3) A poly(alkylene oxide), such as Carbowax 20 M.
(4) A poly(50% methyl/50% -3,3,3-trifluoropropylsiloxane), such as OV-210, OV-202 or SP-2401.
(5) A poly(cyanoalkylsiloxane), such as AN600, OV225, SP2300, or Silar 5CP.

Next the data for characterizing the compounds, and if desired any other data relating to the compound which can form a collection of logically related files, was stored in a computer data base. Preferably the computer is a small desk top or personal computer which is coupled to an input/output apparatus and includes real time operating system software. The input/output apparatus includes at least a keyboard, a CRT screen and a printer, and the computer system software includes a set of programs which can be used to define, create, access and maintain a data base. A suitable computer system can include an IBM Model 50 (System-2) personal computer.

Figure 3A:
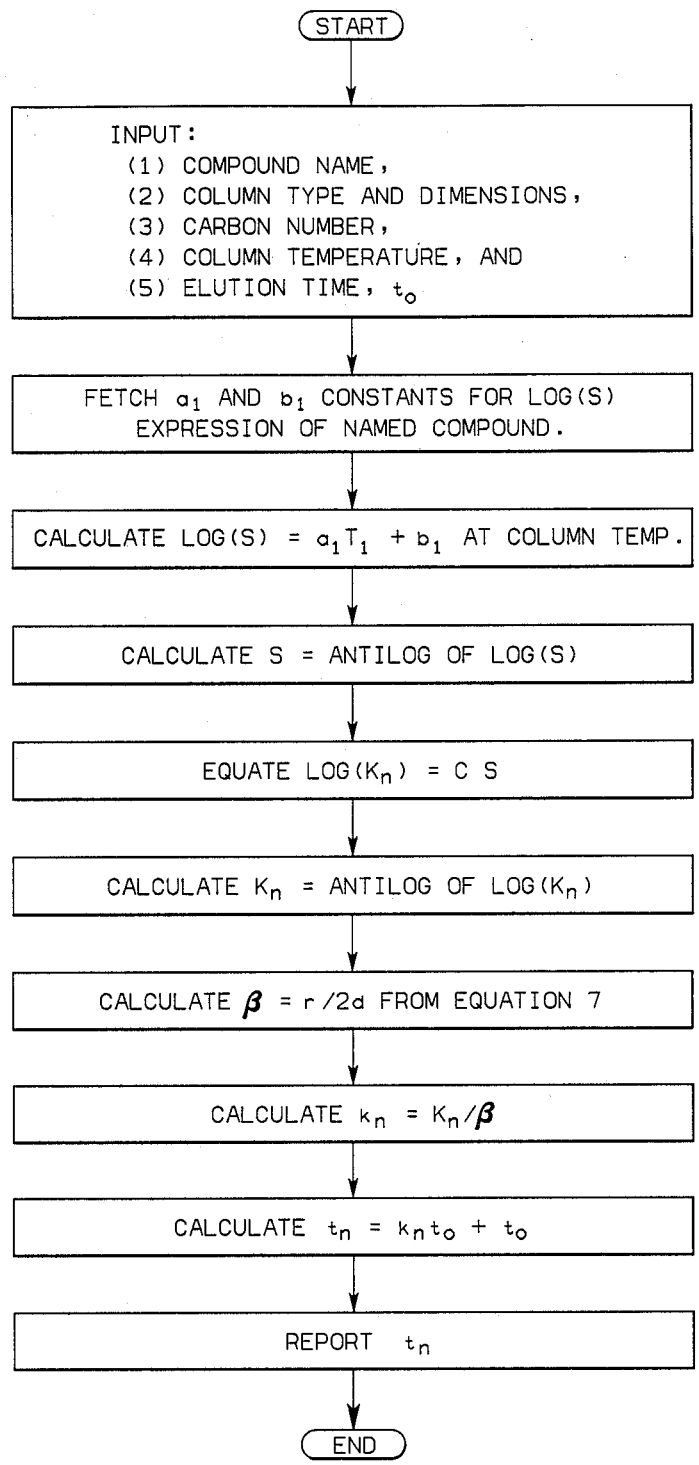
FIG. 3A is a computer flow diagram which illustrates the log (S) method of retrieving elution time from the data base.

Referring now to FIG. 3A, there is illustrated the computer logic to retrieve the elution time of a specified compound through a specified column using the Log (S) characterization of the compound. Essentially a user can request, by inputting required information through a keyboard, the predicted elution time of a compound for a specific column. The computer first fetches the appropriate constants for the named compound that have been prestored in the data base and calculates the log (S) according to equation (1A). In the next step S is calculated by taking the antilog of log (S). Following this step the log ($K_n$) is calculated by multiplying S by the carbon numbers C corresponding to the named compound. Then the antilog of log ($K_n$) yields a value for the distribution coefficient $K_n$. Next the $\beta$ value for the column is calculated according to the equation (7A) or (7B) from the column dimensions, and then the capacity factor $k_n$ for the named compound is calculated according to equation (6). The elution time for the named compound is then calculated according to equation (4). The thus calculated $t_n$ is reported to the user on one of the output devices associated with the computer and can appear as a printed decimal number on the CRT screen or alternately can appear as a tick mark on an appropriately timed graph thus simulating a chromatogram.

Figure 3B:
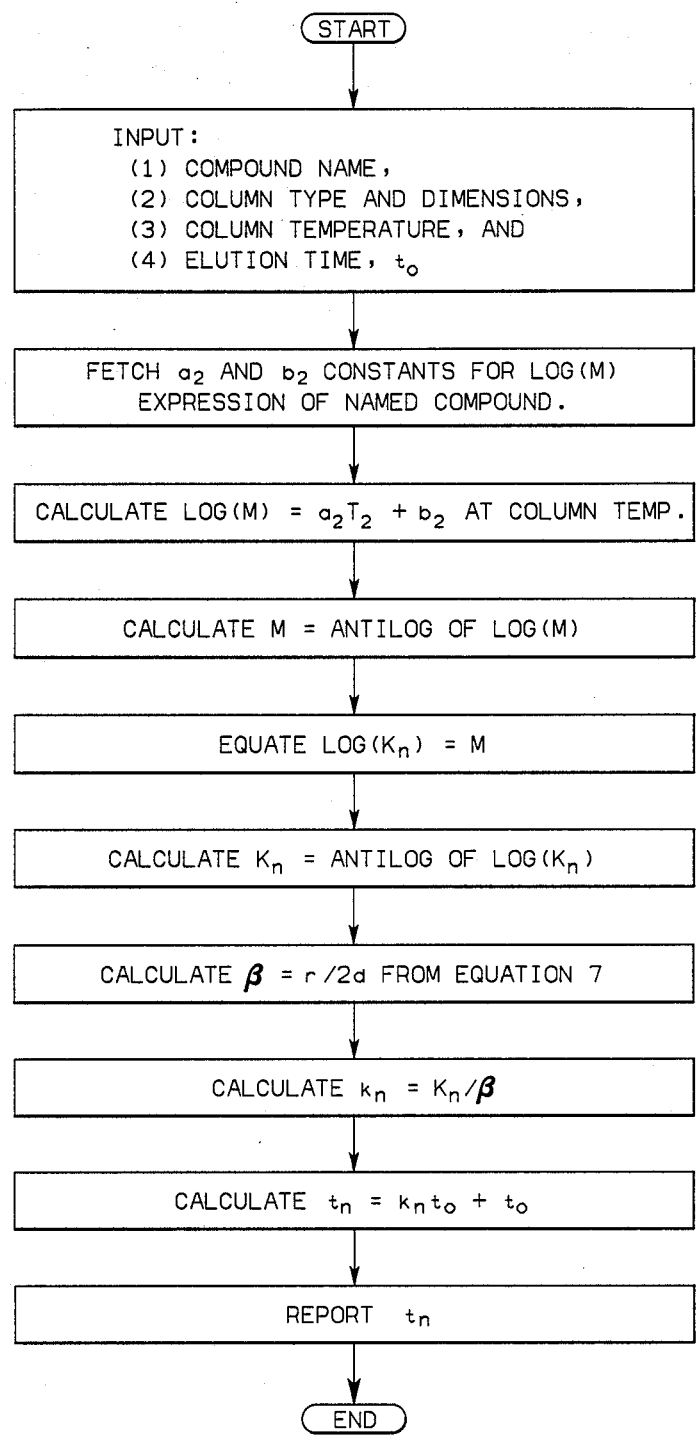
FIG. 3B is a computer flow diagram which illustrates the log (M) method of retrieving elution time data from the data base.

FIG. 3B illustrates the computer logic to retrieve the elution time of a specified compound through a specified column using the Log (M) characterization of the compound. FIG. 3B is similar to FIG. 3A, except that the carbon number is not used in the input statement and the $a_2$, $b_2$ constants are retrieved in place of the $a_1$, $b_1$ constants.

Figure 4A:
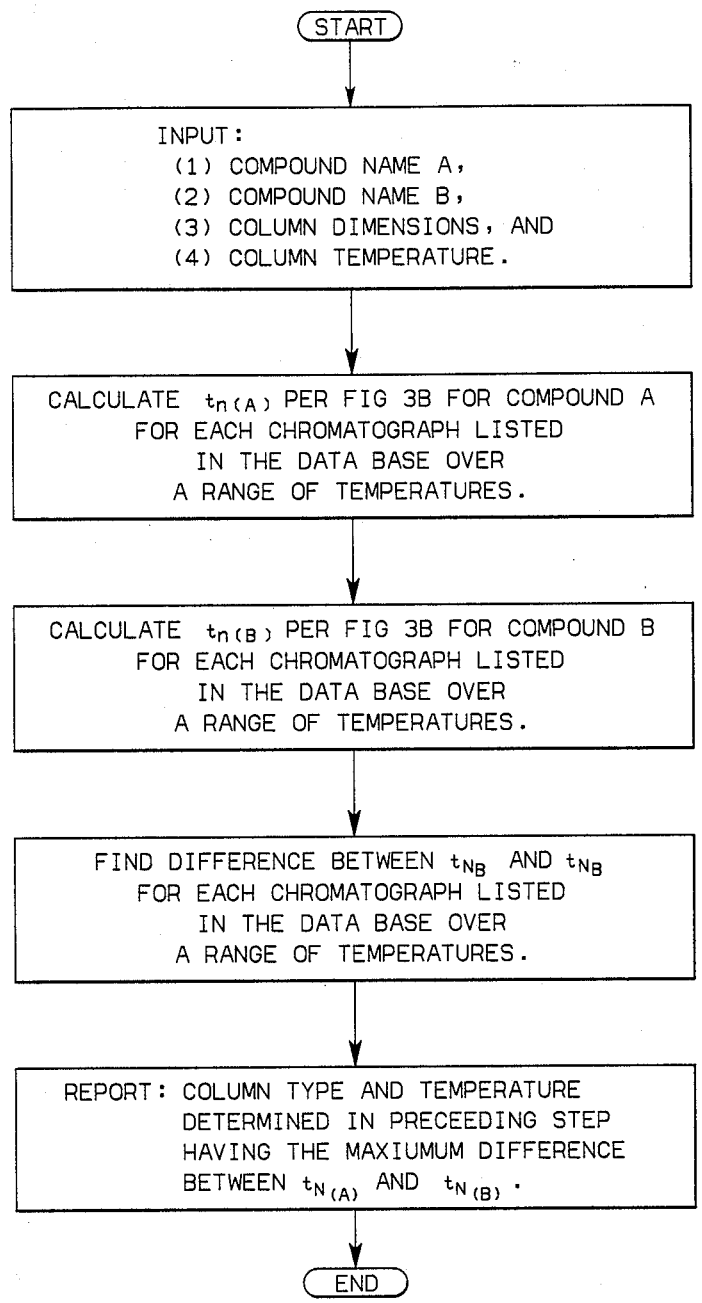
FIG. 4A is a computer flow diagram which illustrates a method of retrieving column information from the data base.

Referring now to FIG. 4A, there is illustrated computer logic to retrieve column-type information from the data base, Essentially an operator can request through a keyboard, the optimum column type for a specific separation of two named compounds. The computer calculates the elution time for each named compound according to one of the methods illustrated in FIG. 3A or 3B, for each stationary phase for which the data base contains characteristic information for that compound. The computer then compares the elution times for each compound to be separated and reports the column type which yields the maximum difference in elution time for the compounds.

Figure 4B:
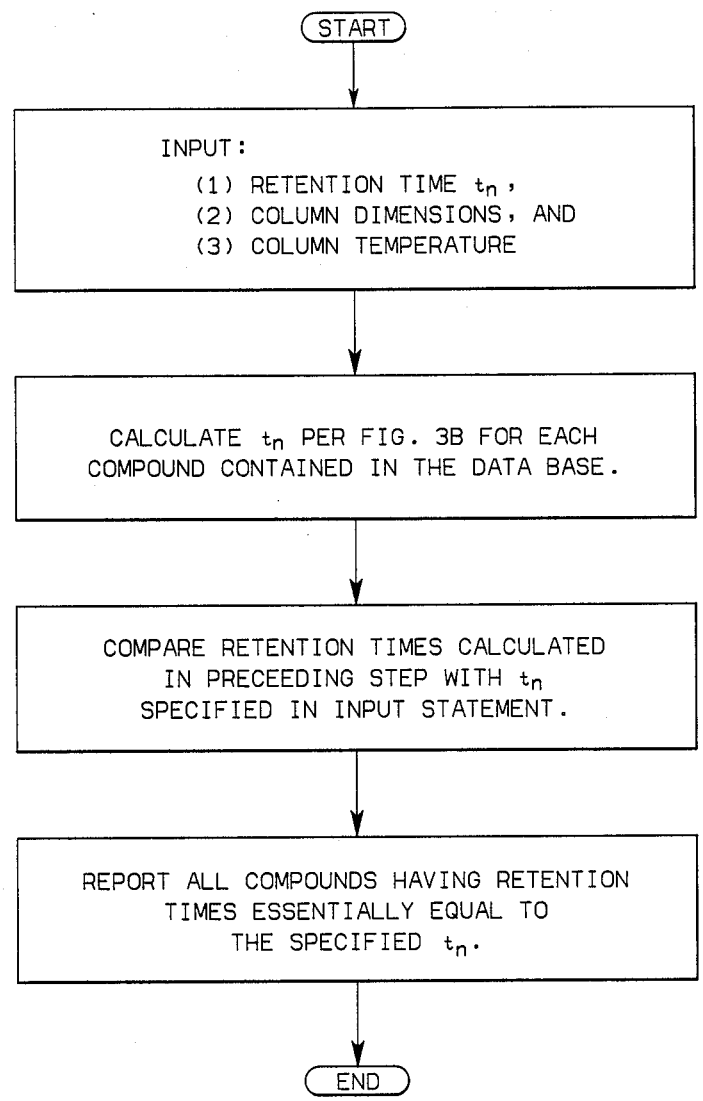
FIG. 4B is a computer flow diagram which represents a method of retrieving compound identification information from the data base.

FIG. 4B, which is similar to FIG. 4A, illustrates computer logic to retrieve compound identification information from the data base.

The identification of an unknown compound from the data base generally requires the use of the log (M) expression since the carbon number for an unknown compound is also an unknown parameter. Therefore, although the log (S) expression may have some advantages, the log (M) form may be the more useful general expression for both the identification of compounds and the prediction of gas chromatographic retention times. Generally, both the log (S) and the log (M) parameters will be stored in the data base file for user convenience.

The invention has been described in terms of the presently preferred embodiment using capillary type columns at a constant temperature as illustrated in FIGS. 1 through 4. However, the log (S) and the log (M) expressions are valid for temperature programmed gas chromatography, where the analyst defines an initial temperature $T_o$ and a temperature rate $R_1$ as illustrated in equation (11) below.

$$T_e = R_1 t_n + T_o \qquad (11)$$

where Te is the final or elution temperature.

The reciprocal of Equation (3) solved for $t_n$ is shown in Equation (12) below:

$$\frac{1}{t_n} = \frac{1}{(1 + k_n)t_o} \qquad (12)$$

Equation (12) represents the fraction of the total retention time on the column corresponding to the distance traveled by a compound at a specific temperature or $K_n$ value. Therefore starting with an initial temperature, $T_o$, and a fixed nonretained peak time, $t_o$ a first value for $K_n$ is calculated according to FIG. 3A or 3B and the corresponding fraction of the total time is then calculated according to Equation (12). This calculation is periodically repeated for example at tenth of a minute intervals and the fractions calculated according to Equation (12) are summed in Equation (13) below.

$$\sum_{T=T_o}^{T=T_e} \frac{1}{(1 + k_n)10t_o} \qquad (13)$$

where $T_o$ and $T_e$ are the initial column temperature and the final column temperature illustrated in Equation (11).

When the various fractional time period summed in Equation (13) total 1, component (n) has traveled the length of the column with the last temperature parameter equal to the elution temperature $T_e$. The factor of 10 appearing in the denominator of Equation (13) converts minutes to tenths of minutes for correspondence with the measurement increments of tenths of a minute utilized for generating new $K_n$ values. Once the $T_e$ value is known, the retention time ($t_n$) is readily obtained from Equation (11).

Table 6 compares the final temperature $T_e$ and the partition ratio $k_n$ predicted according to the method of the present invention with actual temperature program chromatogram for a series of n-alkanes. All of this temperature programmed data was obtained in a 50 meter×0.53 mm i.d. 0V101 column with a $1\times10^{-6}$ film thickness. The initial temperature was 50° C. with a temperature rate of 5° C./min. The comparative data illustrated in Table 5 indicates excellent agreement between predicted and actual results in temperature programmed chromatography.

TABLE 6

Comparison of Elution Characteristic for n-alkanes at R = 5° C./Min.

| Compd. Name | Retent. Time (Min.) | Observed $T_e$ in °C. | Observed $k_n$ | Predicted $T_e$ in °C. | Predicted $k_n$ |
|---|---|---|---|---|---|
| Air | 1.47 | — | — | — | — |
| n-C6 | 2.36 | 61.8 | 0.605 | 61.75 | 0.599 |
| n-C7 | 3.34 | 66.7 | 1.27 | 66.75 | 1.28 |
| n-C8 | 5.09 | 75.4 | 2.46 | 74.75 | 2.37 |
| n-C9 | 7.54 | 87.7 | 4.13 | 86.75 | 4.00 |
| n-C10 | 10.40 | 102.0 | 6.07 | 101.25 | 5.97 |
| n-C11 | 13.38 | 116.5 | 8.10 | 116.25 | 8.01 |
| n-C12 | 16.17 | 130.8 | 10.0 | 130.25 | 9.92 |
| n-C13 | 18.91 | 144.6 | 11.86 | 144.25 | 11.82 |
| n-C14 | 21.52 | 157.6 | 13.64 | 156.75 | 13.52 |

Reasonable variations and modifications of the present invention possible by those skilled in the art are within the scope of the described invention and the appended claims. Since the distribution coefficient, $K_n$, is a true equilibrium constant dependent only on the compound, a modification such as using a packed column is within the scope of this invention. Further, a method for predicting rentention times for use with multicolumn systems such as employing two or more columns in series is within the scope of this invention. Still further, a method for predicting retention times in liquid chromatography wherein the temperature parameter in Equations 1A, 1B, and 8-10 is replaced with a solvent composition factor at a constant temperature is within the scope of this invention.

That which is claimed is:

1. A method of assigning a linear equation to a chemical compound, wherein said compound, in a gaseous state, is separable from other compounds by gas chromatographic techniques, said method comprising the steps of:
    (a) determining the elution time, $t_o$, for a nonretained material eluting from a chromatograph column at a temperature $T_1$;
    (b) determining the elution time, $t_n$, for said compound eluting from said chromatograph column at the temperature $T_1$;
    (c) calculating the distribution coefficient, $K_n$, for said compound in response to the elution time, $t_o$, and the elution time, $t_n$, determined in steps (a) and (b) respectively;
    (d) defining a chromatographic parameter, M, responsive to the distribution constant $K_n$, determined in step (c);
    (e) calculating the log (M) at a temperature $T_1$ to provide a data point for log (M) versus temperature;
    (f) repeating steps (a) through (e) for a desired number of different temperatures;
    (g) determining a least squares fit of a straight line equation for log (M) as a function of temperature, wherein said straight line corresponds to the data obtained in step (f); and
    (h) determining a slope and an intercept of said straight line and assigning the numerical values of said slope and said intercept as a coefficient and a constant term respectively for said linear equation assigned to said chemical compound.

2. A method as recited in claim 1 wherein said chromatograph column is a capillary column having an adsorbent material forming a thin film on the inner surface thereof, and wherein said step of calculating the distribution constant $K_n$, comprises:
    calculating a capacity factor, $k_n$, according to the equation $k_n = (t_n - t_o)/t_o$;
    determining a phase ratio, $\beta$ dependent on the inner radius of said chromatograph column and the film thickness of said adsorbent material; and
    calculating the distribution constant, $K_n$, according to the equation $K_n = k_n \beta$.

3. A method of formatting data related to gas chromatography for utilization in a computer information storage and retrieval system which includes a central processing unit (CPU) with a programmable storage means and having an input/output apparatus associated with said CPU, said input/output apparatus including at least a keyboard and a printer, said method comprising the steps of:
    generating a linear equation of the form $y = mx + b$, wherein said linear equation infers the elution time of a chemical compound in a gas chromatograph as a function of temperature;
    storing the coefficient m and the constant term b of said linear equation and the name of said chemical compound in said programmable storage means in such a manner that the store information can be retrieved;
    inputting to said CPU through said keyboard the name of said chemical compound;
    retrieving, responsive to said step of inputting the name of said chemical compound, said linear equation for said chemical compound for utilization by said CPU; and
    outputting on said output apparatus a visual report related to the elution time of said chemical compound in said gas chromatograph.

4. A method as recited in claim 3, wherein said step of generating a linear equation comprises the following steps:
    (a) determining the elution time, $t_o$, for a nonretained material eluting from a chromatograph column at a temperature $T_1$;
    (b) determining the elution time, $t_n$, for said compound eluting from said chromatograph column at the temperature $T_1$;
    (c) calculating the distribution coefficient, $K_n$, for said compound in response to the elution time, $t_o$, and the elution time, $t_n$, determined in steps (a) and (b) respectively;
    (d) defining a chromatographic parameter, M, responsive to the distribution constant $K_n$, determined in step (c), wherein said chromatographic parameter, M, is representative of the log ($K_n$);
    (e) calculating the log (M) at a temperature $T_1$ to provide a data point for log (M) versus temperature;
    (f) repeating steps (a) through (e) for a desired number of different temperatures; and
    (g) determining a least squares fit of a straight line equation for log (M) as a function of temperature, to generate said linear equation wherein said straight line corresponds to the data obtained in step (f).

5. A method as recited in claim 3 wherein said step of generating a linear equation comprises the following steps;
   (a) determining the elution time, $t_o$, for a nonretained material eluting from a chromatograph column at a temperature $T_1$;
   (b) determining the elution time, $t_n$, for said compound eluting from said chromatograph column at the temperature $T_1$;
   (c) calculating the distribution coefficient, $K_n$, for said compound in response to the elution time, $t_o$, and the elution time, $t_n$, determined in steps (a) and (b) respectively;
   (d) defining a chromatographic parameter S responsive to the distribution constant $K_n$, determined in step (c), and the carbon number C of said compound wherein said chromatographic parameter, S, is representative of the log $(K_n)/C$;
   (e) calculating the log (S) at a temperature $T_1$ to provide a data point for log (S) versus temperature;
   (f) repeating steps (a) through (e) for a desired number of different temperatures; and
   (g) determining a least squares fit of a straight line equation for log (S) as a function of temperature, to generate said linear equation wherein said straight line corresponds to the data obtained in step (f).

6. A method for simulating gas chromatograph characteristics of a chemical compound on a type of column, wherein the simulation occurs in a computer system which includes a central processing unit (CPU) with a programmable storage means and having an input/output apparatus associated with said CPU, said input/output apparatus including, at least, a keyboard and a printer, said method comprising the steps of:
   (a) constructing a data base in said programmable storage means, said data base containing a collection of logically related files which can be jointly searched, said related files including:
      (i) a list of chemical compounds which are separable from a mixture of such compounds by gas chromatographic techniques;
      (ii) a list of gas chromatographs, wherein each gas chromatograph on said list of gas chromatograph employs a different type of column;
      (iii) a list of linear equations, an equation for each compound on said list of chemical compounds for each gas chromatograph on said list of gas chromatographs, wherein each equation on said list of linear equation infers the elution time of a chemical compound on said list of chemical compounds for a gas chromatograph on said list of gas chromatographs as a function of temperature;
   (b) inputting chromatographic parameters to said CPU through said keyboard, wherein the chromatographic parameters are interpreted by said CPU as a request for information;
   (c) retrieving from said programmable storage means in response to said request, at least one designated linear equation from said list of linear equation for use by said CPU;
   (d) determining in said CPU, responsive to said at least one designated linear equation, a characteristic of said chemical compound in said chromatograph so that said CPU predicts said characteristic of said chemical compound in said chromatograph; and
   (e) outputting on said output apparatus a visual report of said characteristic of said chemical compound in said chromatograph.

7. A method as recited in claim 6 wherein said gas chromatograph employs a capillary column having an adsorbent material forming a thin film on the inner surface thereof, and wherein said step of inputting chromatographic parameters to said CPU comprises inputting the following parameters through said keyboard:
   (i) a compound name,
   (ii) a dimension for the inner radius of said capillary column,
   (iii) a dimension for the thickness of said thin film,
   (iv) an elution time $t_o$, for a nonretained material,
   (v) a column temperature, and
   (vi) a type of column, and
   wherein said step of determining in said CPU a characteristic of said compound comprises determining the elution time of said compound in said gas chromatograph; and
   wherein said step of outputting on said output apparatus comprises writing the elution time for an isothermal separation of said compound in said gas chromatograph.

8. A method as recited in claim 7 wherein said step of determining the elution time of said compound in said gas chromatograph comprises:
   fetching in said CPU means a linear equation for said compound name for said type of column having said thin film of adsorbent material on the inner surface thereof;
   calculating, in said CPU, the log (M), from said linear equation for said compound name wherein the log (M) is calculated at said column temperature inputted in paragraph (v),
   calculating, in said CPU, $M = $ antilog log $(M)$,
   equating, in said CPU, $M = \log (K_n)$,
   calculating, in said CPU, $K_n = $ antilog of log $(K_n)$,
   calculating, in said CPU, $\beta = r/2d$ where $r = $ said dimension for radius and $d = $ said dimension for film thickness,
   calculating, in said CPU, $k_n = K_n/\beta$ and
   calculating retention time $t_n = K_n t_o + t_o$.

9. A method as recited in claim 6 wherein said step of inputting chromatographic parameters to said CPU comprises inputting the following chromatographic parameters through said keyboard;
   (1) a compound name,
   (2) a type of column,
   (3) an elution time, $t_o$, for a nonretained material,
   (4) a temperature rate, $R_1$,
   (5) an initial temperature, $T_o$,
   and wherein said step of determining in said CPU a characteristic of said compound comprises determining the elution time of said compound in said gas chromatograph, and wherein said step of outputting on said output apparatus comprises writing the elution time for a temperature programmed separation of said compound in said gas chromatograph.

10. A method as recited in claim 6 wherein said step of inputting chromatographic parameters to said CPU comprises inputting the following parameters through said keyboard:
   (1) a first compound name,
   (2) a second compound name,
   (3) a dimension for said type of column, and (4) a column temperature;

and wherein said step of determining in said CPU a characteristic of said compound comprises determining the type of column having the maximum difference between elution time for said first named compound and said second named compound and wherein said step of outputting on said output apparatus comprises writing the chromatograph type having the maximum difference in elution time between said first compound name and said second compound name.

11. A method as recited in claim 6 wherein said step of inputting chromatographic parameters to said CPU comprises inputting the following parameters through said keyboard:

(1) an elution time $t_n$,
(2) a type of column,
(3) a dimension of said type of column, and
(4) a column temperature, and wherein said step of determining in said CPU a characteristic of said compound comprises determining the compounds having an elution time essentially equal to said elution time, $t_n$, input in paragraph (1), and wherein said step of outputting on said output apparatus comprises writing a list of compounds having an elution time essentially equal to said elution time, $t_n$, input in paragraph (1).

* * * * *